United States Patent
Szopinski

(10) Patent No.: US 6,633,777 B2
(45) Date of Patent: Oct. 14, 2003

(54) APPARATUS FOR EVALUATION OF SKIN IMPEDANCE VARIATIONS

(75) Inventor: Jan Zbigniew Szopinski, 5 Adriaan Crescent, Malanshof, Randburg 2194 (ZA)

(73) Assignees: Aleksander Pastor (PL); Jan Zbigniew Szopinski (ZA)

( * ) Notice: Subject to any disclaimer, the term of this patent is extended or adjusted under 35 U.S.C. 154(b) by 216 days.

(21) Appl. No.: 09/755,640

(22) Filed: Jan. 5, 2001

(65) Prior Publication Data

US 2001/0049479 A1 Dec. 6, 2001

Related U.S. Application Data

(63) Continuation of application No. PCT/ZA99/00048, filed on Jul. 6, 1999.

(30) Foreign Application Priority Data

Jul. 6, 1998 (ZA) ............................................... 98/5900

(51) Int. Cl.⁷ ................................................. A61B 5/05
(52) U.S. Cl. ........................ 600/547; 600/300; 324/692
(58) Field of Search ................................ 600/372, 546, 600/547, 548, 384, 554, 300, 536; 607/2, 75; 128/897, 898, 907, 920; 606/204; 324/600, 605, 609, 692

(56) References Cited

U.S. PATENT DOCUMENTS

| | | | |
|---|---|---|---|
| 3,971,366 A | | 7/1976 | Motoyama |
| 4,016,870 A | | 4/1977 | Lock |
| 4,160,447 A | | 7/1979 | Teshima et al. |
| 4,557,271 A | * | 12/1985 | Stoller et al. ................ 600/547 |
| 4,794,934 A | * | 1/1989 | Motoyama et al. ......... 600/547 |
| 5,409,011 A | * | 4/1995 | Alexeev et al. ............. 600/547 |
| 5,678,547 A | * | 10/1997 | Faupel et al. ............... 600/409 |
| 5,732,710 A | * | 3/1998 | Rabinovich et al. ........ 600/547 |
| 6,285,905 B1 | * | 9/2001 | Chiang et al. ................ 607/2 |

FOREIGN PATENT DOCUMENTS

| | | | | |
|---|---|---|---|---|
| DE | 19911200 A1 | * | 9/2000 | ............ A61B/5/05 |
| RU | 2126675 C1 | * | 2/1999 | .......... A61H/39/00 |
| WO | WO 91/11957 | | 8/1991 | |
| WO | WO 98/26714 | | 6/1998 | |

* cited by examiner

*Primary Examiner*—Max F. Hindenburg
*Assistant Examiner*—Charles A Marmor, II
(74) *Attorney, Agent, or Firm*—Akerman Senterfitt

(57) ABSTRACT

The invention provides an apparatus and method for automatic evaluation of skin resistance or impedance variations in order to diagnose the state of health of at least a portion of a human or animal body. The difference between an AC impedance measured at a specific frequency and at a specific skin area with calibration electrode and a reference electrode and the impedance measured at a similar frequency and in the same area with a measurement electrode and a reference electrode, is used to determine the state of health of the internal organ corresponding to the examined skin area. Alternatively, the skin between the electrodes is exposed to a DC potential of a magnitude selected to give a breakthrough effect. The resistance of the skin is measured between a measurement electrode polarised negatively with respect fo a reference electrode, and the DC resistance of the same skin area is again measured but with the measurement electrode polarised positively with respect to the reference electrode. The ratio of these two values is used to determine the state of health of the internal organ corresponding with the examined skin area.

15 Claims, 13 Drawing Sheets

APPARATUS FOR EVALUATION OF SKIN IMPEDANCE VARIATIONS

This application is a continuation of PCT/2A99/00048 filed Jul. 6, 1999.

COPYRIGHT NOTICE

The matter contained herein is subject to Copyright protection in Berne Convention countries, which copyright is the property of the inventor. Publication of the patent specification, or any act by any patent office, does not constitute a waiver of these rights.

BACKGROUND TO THE INVENTION

This invention relates to an apparatus and method for automatic evaluation of skin impedance variations in order to estimate the state of health of the internal organs of a human or animal.

Existing methods of utilising skin impedance values for organ diagnostics base their results on non-ratiometric measurements of basic skin impedance and produce inconsistent and unreliable results which depend on numerous variables, including the emotional state of the patient, muscular tension, measurement time, the contact area and pressure of the measuring electrode and various physiological differences between individuals.

After many years of research the inventor now believes that the internal organs of the body of a human or animal have corresponding areas on the skin where information regarding the corresponding internal organs can be retrieved by measuring the electrical properties of said skin. The inventor further believes that said corresponding areas of the skin have other properties related to the science of reflexive pyhsiotherapy (including acupuncture), for example, the ability to heal and/or relieve pain caused by the corresponding organs.

The inventor believes yet further that these corresponding areas of the skin may be mapped, which map is applicable to various individuals.

The inventor has found that the ear auricle may be particularly accurately mapped and is most suitable for the method of the invention since in most cultures the skin of the ear is exposed and may be examined without any garments having to be removed.

In this specification, unless the context clearly indicates to the contrary, the term "impedance", is to be understood to include resistance.

SUMMARY OF THE INVENTION

The impedance variation can be measured in two ways:
Method 1. AC Evaluation

The difference between the AC impedance measured at a specific frequency and at a specific skin area with a calibration electrode and a reference electrode and the impedance measured at a similar frequency and in the same area with a measurement electrode and a reference electrode, is used to determine the state of health of the internal organ corresponding to the examined skin area. The calibration electrode and reference electrode contact areas are relatively larger than the measurement electrode skin contact area.
Method 2: DC Evaluation The term "break-through effect" refers to the sudden and significant drop in skin electrical resistance witnessed after a sufficient potential difference is applied between the electrodes.

The skin between the electrodes is exposed to a DC potential of a magnitude selected to give the break-through effect. The DC resistance of the skin is measured between a measurement electrode polarised negatively with respect to a reference electrode, and the DC resistance of the same skin area is again measured but with the measurement electrode polarised positively with respect to the reference electrode. The ratio of these two values is used to determine the state of health of the internal organ corresponding with the examined skin area.

An apparatus broadly in accordance with the invention may include the following functional blocks:

A measurement and/or calibration electrode, a reference electrode, a voltage generator block, a measurement block, a control block, a user interface block, a result presentation block and, optionally, a data storage block.

The voltage generator block generates a potential difference between the measurement electrode and the reference electrode, or the calibration electrode and the reference electrode. The voltage generator block is connected to and controlled by the control block. The measurement block is connected to the measurement electrode and the reference electrode (FIG. 1).

The measurement block determines the impedance between the measurement electrode and the reference or calibration electrode. Alternatively the voltage generator block can be connected through the measurement block to the measurement electrode or the reference electrode (FIG. 2). The ultimate purpose of the measurement block is to measure a parameter (such as voltage or current) that can be used to determine the impedance or resistance between the measurement electrode and the reference electrode. The measurement block is connected to the control block.

The control block is connected to the user interface block (if present), the data storage block (if present), the result presentation block, the voltage generator block and the measurement block. The control block sets the voltage generated by the voltage generator block. The control block uses information received from the measurement block to detect the break-through effect, and the resistance asymmetry. The control block can store and retrieve information in the data storage block (if present). The control block informs the user of the results of the measurements through the result presentation block. The result presentation block may be generate a visual or audio indication to inform the user of the result i.e. the state of health of the internal organ obtained by the control block.

According to an aspect of the invention, there is provided an apparatus for diagnosing a state of health of an organ in a human or animal body, the apparatus including an electrical signal generator, a calibration electrode, and a measurement electrode for connection in use to the generator. One of the calibration and measurement electrodes is a point electrode having a small skin-contactable surface area, and the other electrode, respectively, has a significantly larger skin-contactable surface area than the point electrode. Also included is recording means configured to record a first measured value of a first parameter which is dependent on the resistance or impedance between the calibration and reference electrodes when the calibration electrode is placed in contact with a first zone of skin corresponding to the organ and the reference electrode is placed in contact with another one on the body. An AC potential difference is applied in use between the calibration and reference electrodes by the generator. Recording means is configured to record a second measured value of a second parameter which is dependent on the resistance or impedance between the measurement and reference electrodes when the calibration electrode has been replaced by the measurement electrode and the same AC potential difference is applied between the measurement and reference electrodes. Means for comparing the first and second measured values to obtain a third value is also included, which is an indicator of the state of health of the organ to which the first zone of skin corresponds.

The frequency of the AC signal is typically about 250 Hz.

The apparatus may include a display means for indicating the first zone of skin onto which the calibration and measurement electrodes should be placed in order to obtain a diagnosis for a particular organ. The display means typically indicates zones of skin which are located on a foot or an ear.

The third value may be expressed as a ratio of the first and second measured values.

The apparatus may include communication means for communicating, to an operator of the apparatus, the state of health of the diagnosed organ as being either healthy, normal, sub-acute or acute, depending on the third value.

According to another aspect of the invention, there is provided a method for diagnosing a state of health of an organ in a human or animal body. The method includes the steps of placing a calibration electrode on or near a zone of skin which corresponds to the organ and placing a reference electrode in contact with another zone of skin which corresponds to the organ and placing a reference electrode in contact with another zone of skin on the same body. A first measured value of a first parameter is recorded, which is dependent on the resistance or impedance between the calibration and reference electrodes when an AC potential difference is applied between the calibration and reference electrodes. The calibration electrode is replaced with a measurement electrode. One of the calibration and measurement electrodes is a point electrode having a small skin-contactable surface area, and the other electrode, respectively, has a significantly larger skin-contactable surface area than the point electrode. A second measured value of a second parameter is recorded, which is dependent on the resistance or impedance between the measurement and reference electrodes when the same AC potential difference is applied between the measurement and reference electrodes. The first and second measured values are compared to obtain a third value which is an indicator of the state of health of the organ to which the first zone of skin corresponds.

The frequency of the alternating current while obtaining the first and second values is typically about 250 Hz.

The third value may be expressed as a ratio of the first and second values.

The measurement electrode may be placed on an outer ear, or on a sole of a foot, having the zone of skin which corresponds to the organ.

The method may include the step of using a display means to indicate the zone of skin of a foot or an ear onto which the measurement electrode should be placed in order to obtain a diagnosis for a particular organ.

DESCRIPTION OF OPERATION

After a great deal of experimental work the inventor has found that an apparatus broadly in accordance with the invention may be operated as described below to obtain reliable results.

Technique 1: AC Evaluation

The calibration electrode is placed in contact with the relevant skin area corresponding to the internal organ of a subject the sate of health of which is to be determined. The reference electrode is placed in contact with any other skin area, usually the hand of the subject. The control block uses the voltage generator block to generate an AC signal of specific frequency and magnitude between the calibration and reference electrodes. The control block determines the impedance between the electrodes via the measurement block. The control block stores the impedance value in the data storage block (referred to as "calibration impedance"). The control block signals that the calibration impedance has been determined via the result presentation block. The calibration electrode is removed and the measurement electrode is placed on the skin area undergoing investigation. The control block uses the voltage generator block to generate an AC signal of similar frequency and magnitude between the calibration and reference electrodes.

The control block determines the ratio between the calibration impedance and the impedance measured with the measuring electrode and converts this ratio to an indication of the state of health of the internal organ. The control block displays the result on the result presentation block (e.g. on a disease intensity percentage scale).

Conveniently the result is displayed in percentage format, calculated according to the following equation:

$$\% \text{ Disease} = (1 - I_{measurement}/I_{reference}) \times 100;$$

or $$\% \text{ Disease} = (1 - R_{reference}/R_{measurement}) \times 100$$

Various percentage ranges corresponding to different states of health of the organ. Typically 0 to 40% indicates a healthy state, 40 to 60% indicates the upper limits of the healthy state, 60 to 80% indicates a sub-acute state, and 80 to 100% indicates an acute condition of the internal organ in question.

Technique 2: DC Evaluation

The reference electrode is placed in contact with any skin area. The measurement electrode is placed in contact with a specific skin spot corresponding with an internal organ the state of health of which is to be determined. The control block uses the voltage generator block to generate a DC potential difference between the electrodes. The control block determines the resistance between the electrodes via the measurement block. The control block adjusts the DC potential difference and checks the resistance until the resistance falls below a certain threshold or suddenly starts decreasing rapidly (break-through effect). The control block checks the resistance until a stable value is reached. The control block stores this resistance value in the data storage block (referred to as "reference resistance").

The control block inverts the polarisation of the measurement and reference electrodes with respect to each other and uses the voltage generator block to apply a DC potential across the electrodes. The control block determines the resistance between the electrodes via the measurement block (referred to as "measurement resistance").

The control block determines the ratio between the "measurement resistance" and the "reference resistance" and calculates the intensity of disease from this ratio. The following equation is used for the calculation:

$$\% \text{ Disease} = (1 - I_{measurement}/I_{reference}) \times 100;$$

or $$\% \text{ Disease} = (1 - R_{reference}/R_{measurement}) \times 100$$

The control block displays the result on the result presentation block (e.g. on a disease intensity percentage scale).

Conveniently the result is displayed in percentage format, with various percentage ranges corresponding to different state of health of the organ. Typically 0 to 40% indicates a healthy state, 40 to 60% indicates the upper limits of the healthy state, 60 to 80% indicates a sub-acute state, and 80 to 100% indicates an acute condition of the internal organ in question.

For best break-through effect induction the reference resistance measurement should be made with the measurement electrode polarised negatively with respect to the reference electrode, although with higher potential differences between the electrodes it is believed that the breakthrough effect may also be observed if the polarity is inverted.

When using the DC technique, if the internal organ is not healthy a higher resistance will be measured with the measurement electrode polarised positively with respect to the reference electrode than with the measurement electrode polarised negatively with respect to the reference electrode e.g. 300 kΩ as opposed to 30 kΩ. Similarly, when using the AC technique, the measurement obtained using the measurement electrode will have an impedance reading which is higher than that of the measurement obtained using the calibration electrode.

It is also possible to use an AC signal when using the DC technique.

Although both the AC and DC evaluation techniques are effective, for thin skin regions of the body, such as the ear auricle, the DC evaluation technique is preferred, while for thicker skin areas of the body, such as the feet, the AC method is preferred as thicker skin areas require higher voltages for the breakthrough effect to occur, which could be painful for the subject.

The inventor believes that an apparatus such as that described above, uses new measurement technologies and ratiometric techniques and achieves consistent and repeatable diagnostic results which are independent of various physiological differences between individuals, the emotional state of a patient, muscular tension and the measurement time. The results depend on the intensity of the disease, the effect of pressure is insignificant.

EXAMPLES

Example 1:

In a first test in which a gastric ulcer was diagnosed, the following results were obtained:

Auricular projection areas (thin skin—DC measurement):
  reference resistance=10 kΩ;
    Stomach projection area: measurement resistance=200 kΩ; i.e. 95% of disease activity
    Healthy organ projection areas: measurement resistance=10–25 kΩ i.e. 0–60% of disease activity Pedal projection areas (thick skin—AC measurement):
  Reference resistance=15 kΩ(at 250 Hz)
    Stomach projection area: measurement resistance=300 kΩ i.e. 95% of disease activity
    Healthy organ projection areas: measurement resistance=15–37.5 kΩ i.e. 0–60% of disease activity Example 2:
Pyelonephritis (Kidney Infection)
  Auricular projection areas (thin skin—DC measurement):
    Reference resistance=10 kΩ
      Kidney projection area: measurement resistance=100 kΩ i.e. 90% of disease activity
      Healthy organ projection areas: measurement resistance=10–25 kΩ i.e. 0–60% of disease activity Pedal projection areas (thick skin—AC measurement):
    Reference resistance=10 kΩ(at 250 Hz)
      Kidney projection area: measurement resistance=100 kΩ i.e. 90% of disease activity
      Healthy organ projection areas: measurement resistance=10–25 kΩ i.e. 0–60% of disease activity

Figure 1:
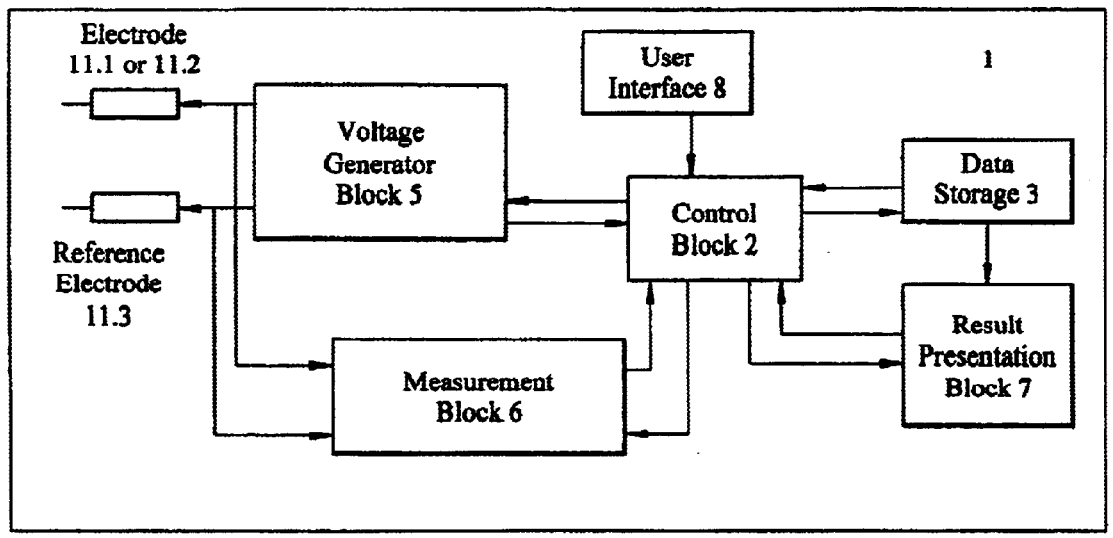
FIG. 1 shows, in schematic block diagram representation, an apparatus for evaluation of skin impedance variations and state of health of a corresponding internal organ, using the DC or AC technique of measurement, broadly in accordance with the invention.

In the figures reference numeral 1 broadly indicates an apparatus for determining the state of health of an internal organ of a subject by the impedance variation evaluation method, broadly in accordance with the invention The apparatus 1 includes a voltage generator block 5 which generates a potential difference between a measurement 11.1 or calibration 11.2 electrode and a reference electrode 11.3. The voltage generator block 5 is connected to and controlled by the control block 2. The measurement block 6 is connected to the measurement electrode 11.1 or calibration electrode 11.2 and the reference electrode 11.3.

Figure 2:
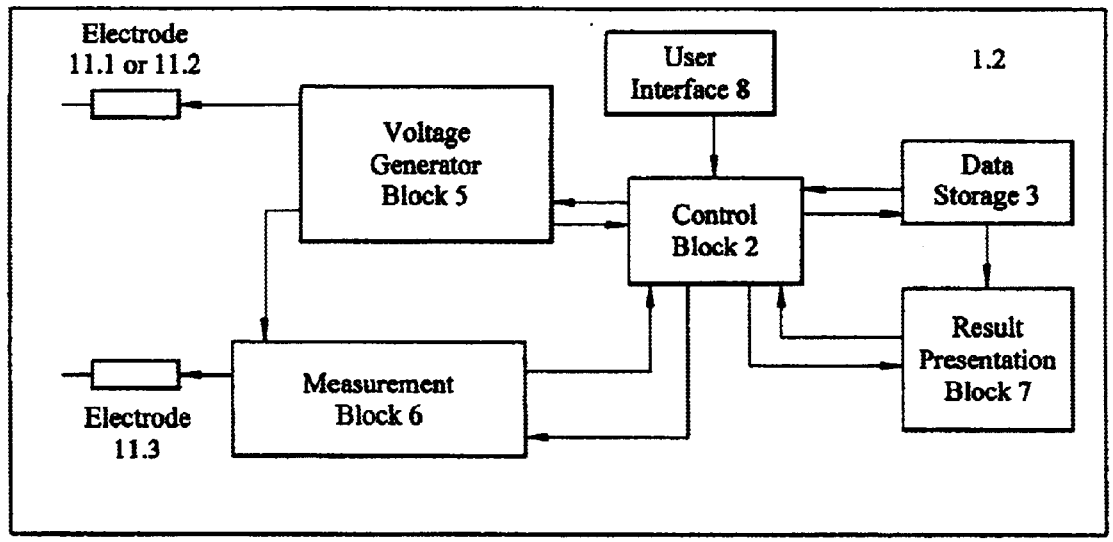
FIG. 2 shows, in schematic block diagram representation, an alternative implementation of an apparatus for evaluation of skin impedance variations and state of health of a corresponding internal organ, using the DC or AC technique of measurement, broadly in accordance with the invention.

In FIG. 2 reference numeral 1.2 broadly indicates an alternative apparatus for determining the state of health of an internal organ of a subject by the impedance variation evaluation method, broadly in accordance with the invention.

The voltage generator block 5 generates a potential difference between the measurement 11.1 or calibration electrode 11.2 and the reference electrode 11.3. The voltage generator block 5 is connected to and controlled by the control block 2. The measurement block 6 is connected to the measurement electrode 11.1 or calibration electrode 11.2 and the reference electrode 11.3.

The measurement block 6 determines the impedance between the measurement electrode 11.1 or calibration electrode 11.2 and the reference electrode 11.3. Alternatively the voltage generator block 5 can be connected through the measurement block 6 to the measurement electrode 11.1 or the calibration electrode 11.2 or the reference electrode 11.3. The ultimate purpose of the measurement block 6 is to measure a parameter (such as voltage or current) that is dependent on the impedance or resistance between the measurement electrode 11.1 or calibration electrode 11.2 and the reference electrode 11.3. The measurement block 6 is connected to the control block 2.

The control block 2 is connected to the user interface block 8, the data storage block 3, the result presentation block 7, the voltage generator block 5 and the measurement block 6. The control block 2 sets the voltage generated by the voltage generator block 5. The control block 2 uses information received from the measurement block 6 to detect the breakthrough effect and the resistance asymmetry. The control block 2 can store and retrieve information in the data storage block 3. The control block 2 informs the user of the results of the measurements through the result presentation block 7. The result presentation block 7 may generate a visual or audio indication to the user of the result i.e. the state of health of the internal organ, obtained by the control block 2.

Figure 3:
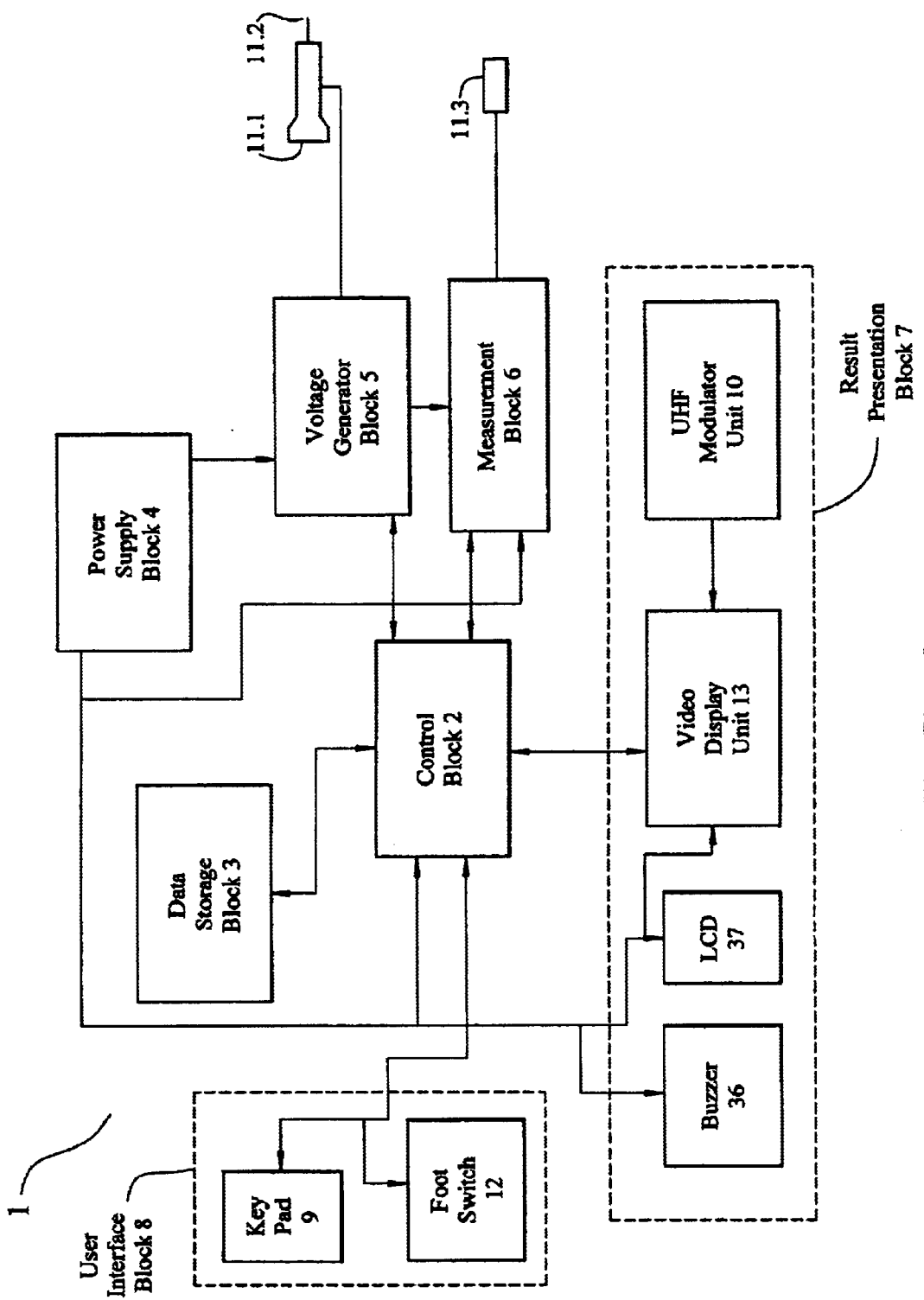
FIG. 3 shows, in schematic block diagram representation, an apparatus for evaluation of skin impedance variations and state of health of a corresponding internal organ, using the DC or AC technique of measurement, in accordance with the invention.
Figure 4:
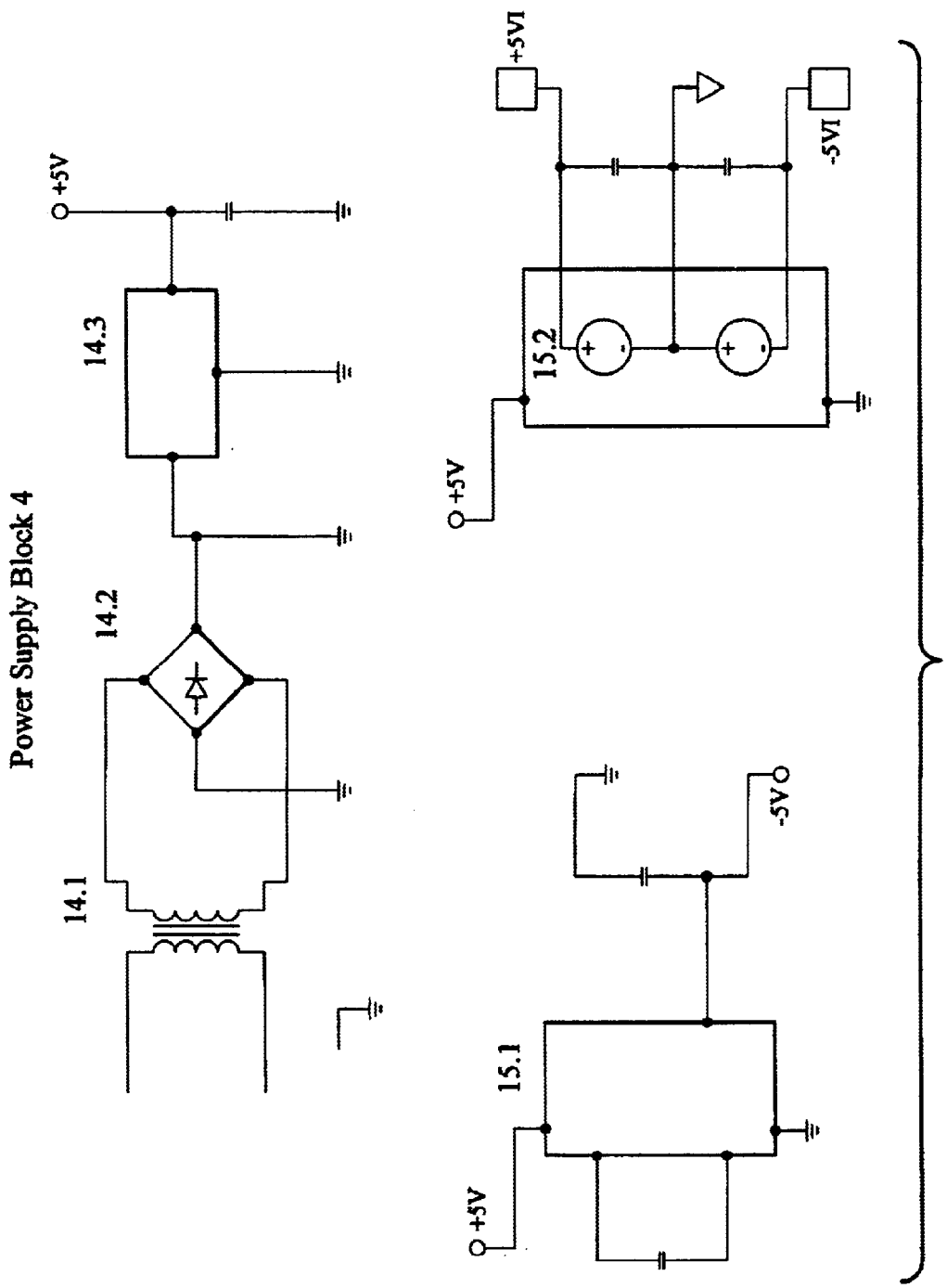
FIG. 4 shows, in schematic circuit diagram representation, a power supply unit according to FIG. 3.
Figure 5:
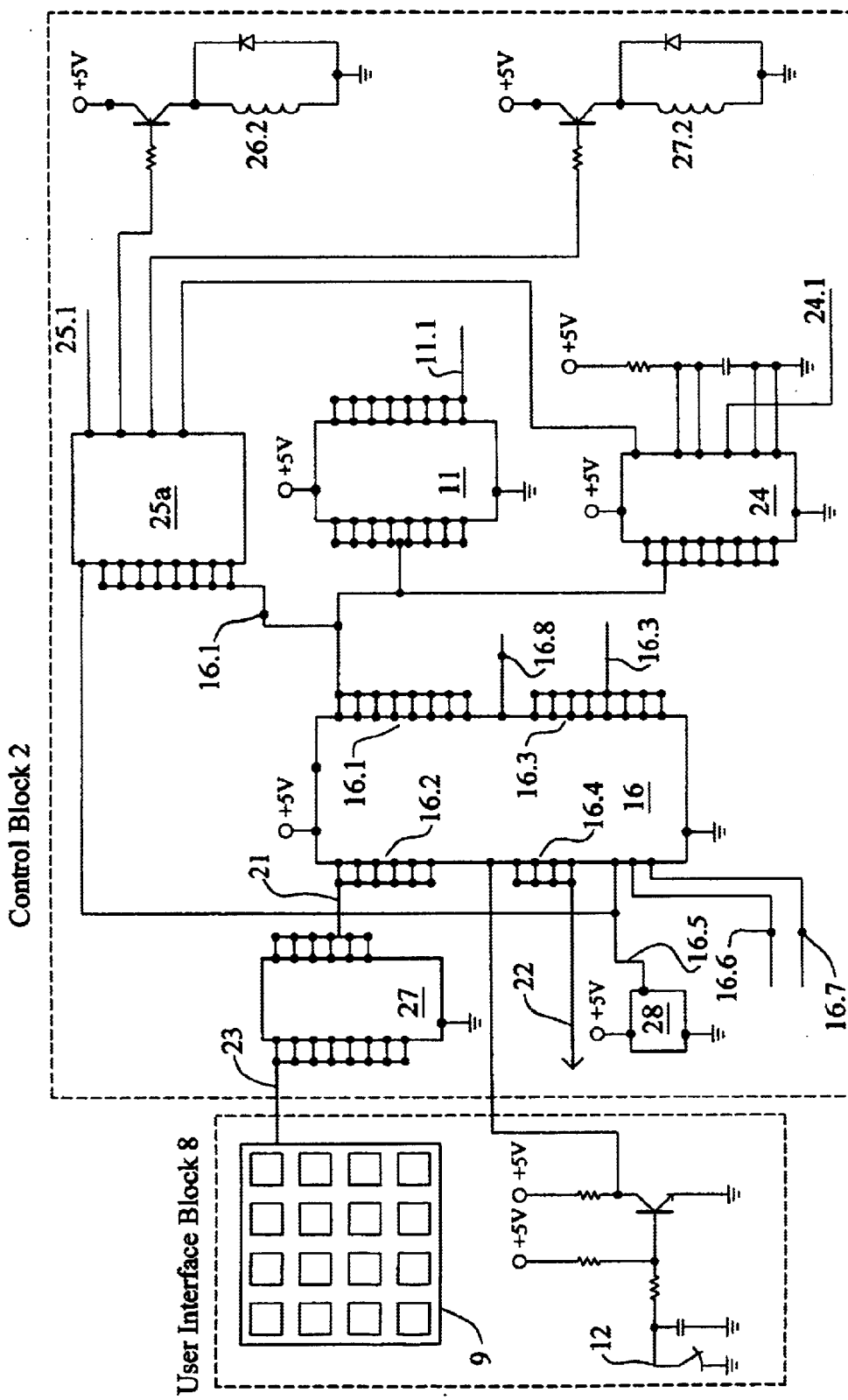
FIG. 5 shows, in schematic circuit diagram representation, a control block and a user interface block according to FIG. 3.
Figure 6:
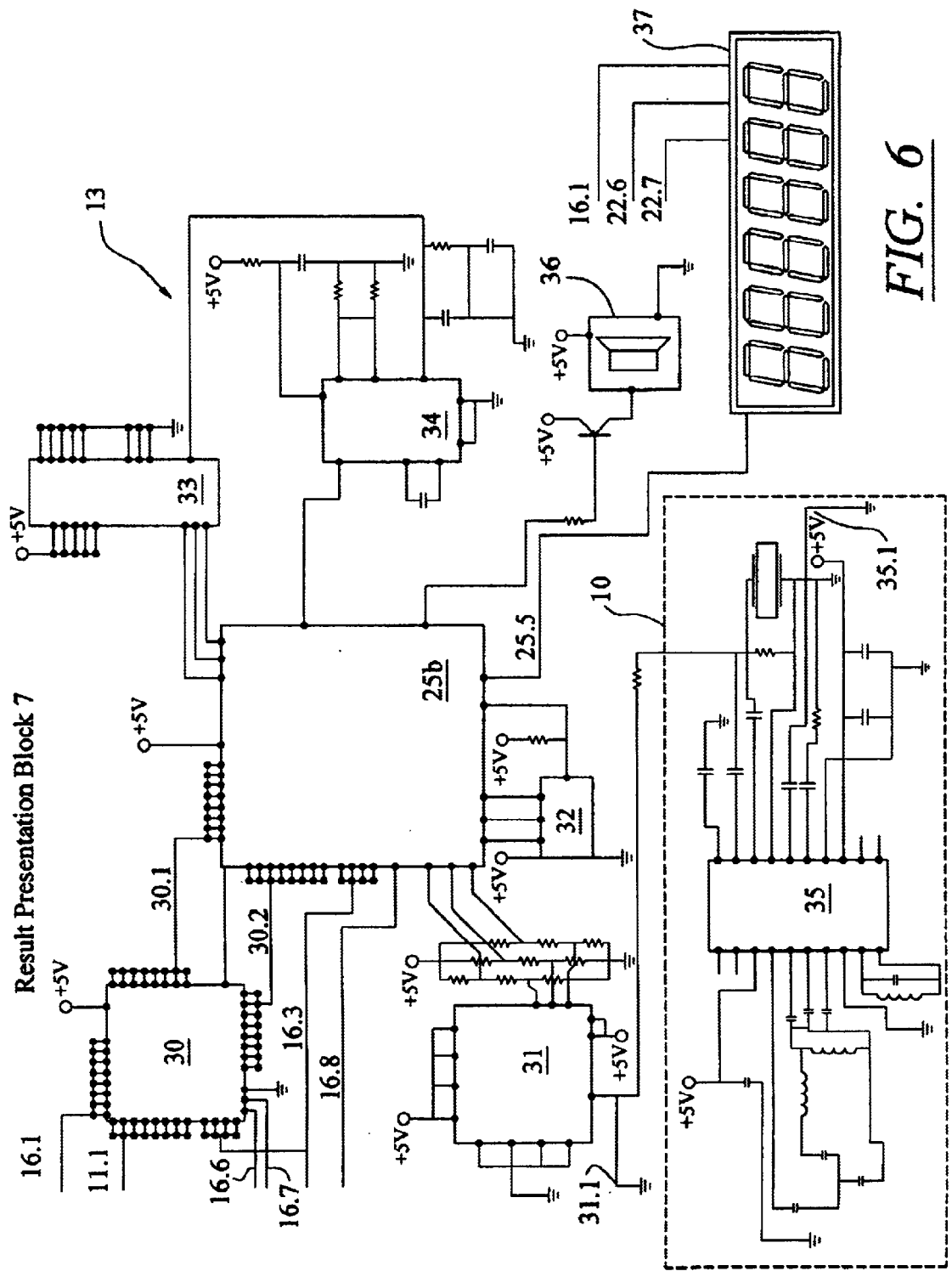
FIG. 6 shows, in schematic circuit diagram representation, a result presentation block according to FIG. 3.
Figure 7:
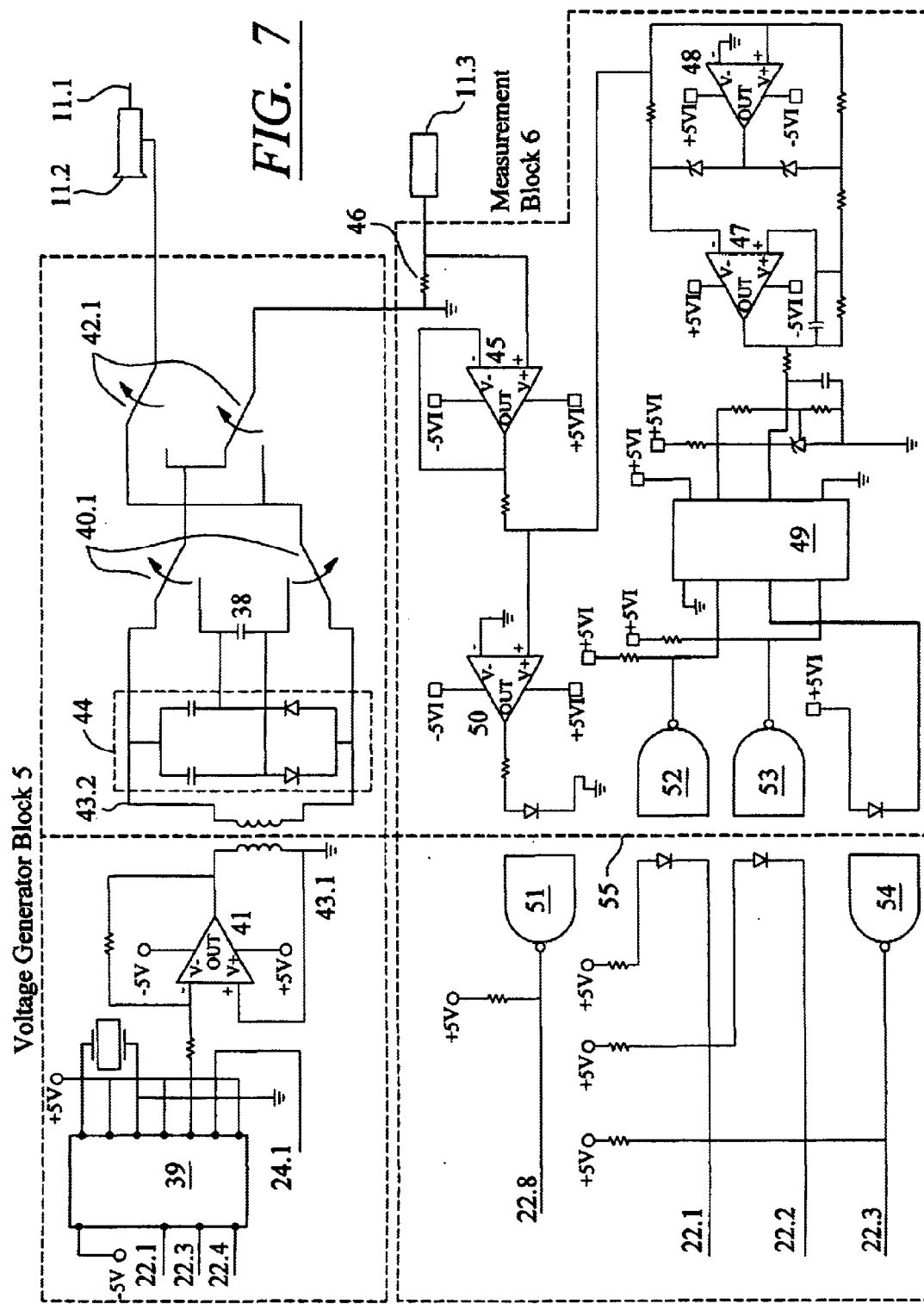
FIG. 7 shows, in schematic circuit diagram representation, a voltage generator block and a measurement block according to FIG. 3.
Figure 8:
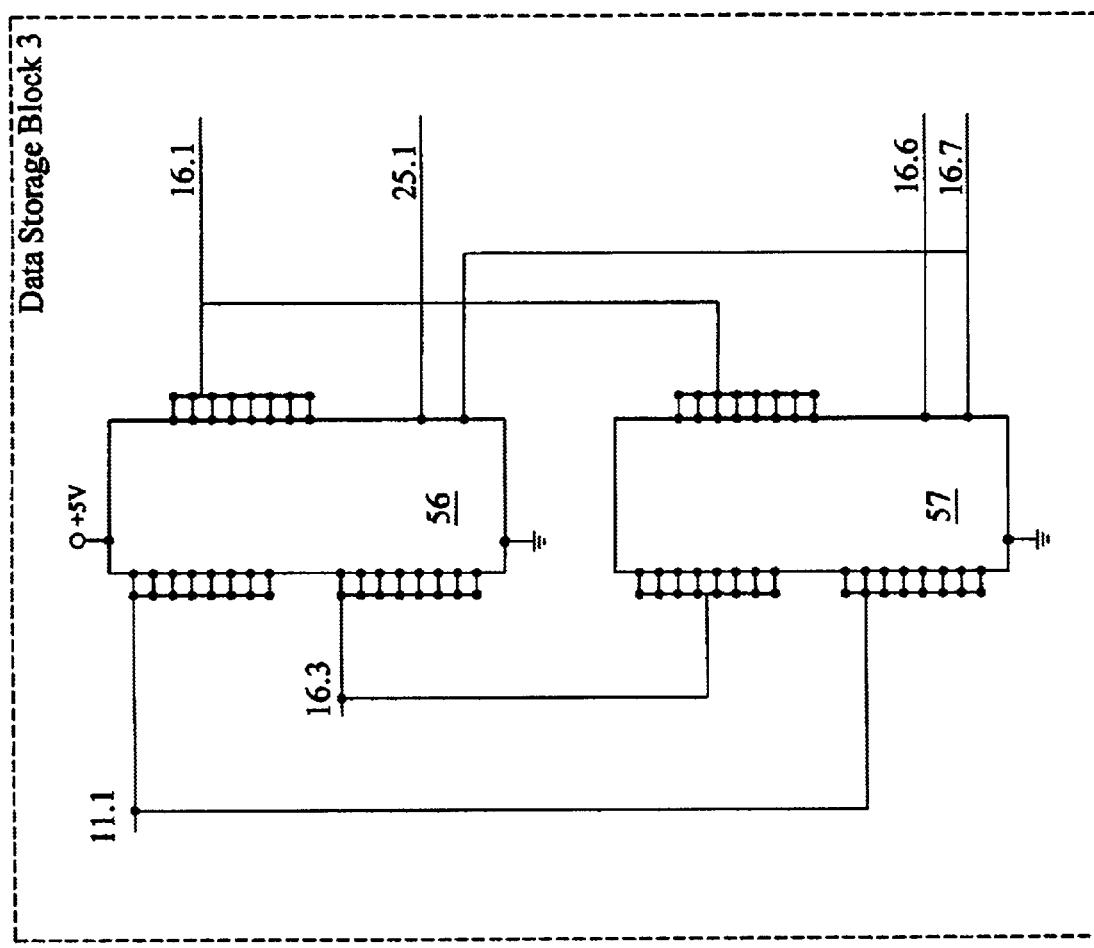
FIG. 8 shows, in schematic circuit diagram representation, a data storage block according to FIG. 3.

Referring to FIG. 3, an electrodermal diagnostic unit 1 is provided which is primarily intended for use in diagnosing internal organ pathology in humans through electric stimulation and impedance measurement of remotely located skin spots.

In the electrodermal diagnostic unit 1 the control block 2 displays instructions to the operator through LCD display 37 exclusively or in combination with a video monitor connected to the video display unit 13 or a television set connected to the UHF modulator unit 10. Lists of organs that can be diagnosed are displayed on the monitor or television set. The operator selects internal organs to diagnose via the keypad 9.

The control unit 2 selects a method of diagnosis based on the location of the skin spot/zone to be investigated. Two methods of diagnosis, are available specifically alternating current measurement (AC measurement) or direct current measurement (DC measurement). AC measurement is better suited to areas with thicker skin such as the soles of the feet. DC measurement is better suited to areas with thin skin such as the ear.

The control unit 2 displays a picture of the region to be investigated (such as the foot or ear). A flashing zone or spot indicates where the measuring electrode 11.1 must be placed by the operator. The control unit 2 controls the voltage generator block 5 through an optical link to execute the selected test.

Figure 9:
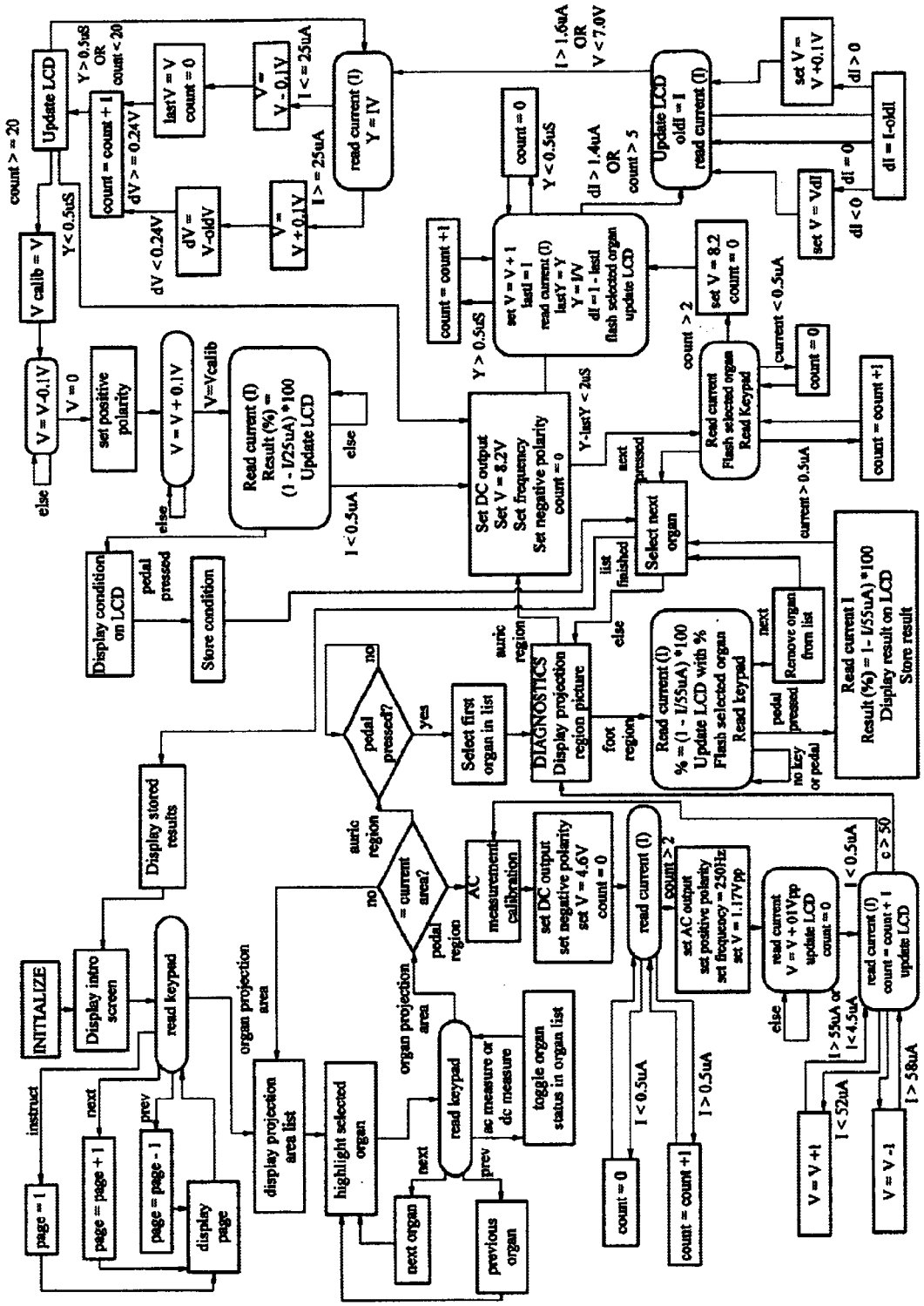
FIG. 9 shows a simplified flow diagram of the software used in the microcontroller in the control block in FIG. 5.

For DC measurement: The voltage generator block 5 generates a small constant potential difference between the measurement electrode 11.1 and the reference electrode 11.3, with the measurement electrode polarized negatively with respect to the reference electrode. The current is continuously monitored by the control block 2 using the measurement block 6 and when the current rises above a preset threshold, it is assumed that both probes are in contact with the skin. The potential difference between the probes is slowly increased and the current through the probe measured continuously. The skin resistance is calculated by dividing the value of the potential applied to the probes by the value of the measured current running through the probes. When a sudden significant drop in this resistance is detected (see FIG. 9 for algorithm) the potential difference between the probes is continuously adjusted so as to maintain the measured current through the probes at a predetermined level. This continues until the rate of change in skin resistance falls below a predetermined level. The value of the potential difference at this time is stored by the control block 2 in the data storage block 3. The control block 2 uses the voltage generator block to apply the same potential difference between the probes with opposite polarization (the measurement electrode positively polarized with respect to the reference electrode). The current is continuously measured. The ratio (measured current)/(preset current) is believed to give an indication of the degree of pathology in a particular organ. If this ratio is close to zero, the relevant organ is believed to be diseased. If this ratio is greater than 0.6 then the relevant organ is believed to be healthy. The closer this ratio is to zero, the greater the degree of pathology (e.g. cancer) is believed to be present in the organ.

The control block 2 monitors the current via the measurement block 6 and displays the test result on the LCD display 37 on a disease percentage scale until the operator presses the foot pedal 12. The control block stores the test result in the data storage block 3, and activates the buzzer 36 to indicate the completion of the test.

For AC measurement: The operator places the reference electrode 11.3 and the calibration electrode 11.2 on the skin of the subject when prompted via the LCD display 37. The voltage generator block 5 generates a small constant potential difference between the electrodes 11.2,11.3. The current is continuously monitored and when the current rises above a preset threshold, it is assumed that both probes are in contact with the skin. An sinusoidal alternating voltage is now applied between the electrodes. The current is monitored continuously by the control block 2 using the measurement block 6 and the voltage adjusted until the current reaches a preset level. This process is referred to as calibration The control unit 2 displays a picture of the region to be investigated (typically the foot) on the video monitor or television screen using the result presentation block. The control unit 2 displays a message on the LCD display 37 informing the operator that the measuring electrode 11.1 and the reference electrode 11.3 must now be used. A flashing zone or spot indicates where the measuring electrode 11.1 must be placed by the operator. The current is continuously measured. The ratio (measured current)/(preset current) is believed to give an indication of the degree of pathology in a particular organ. If this ratio is close to zero, the relevant organ is believed to be diseased. If this ratio is greater than 0.6 then the relevant organ is believed to be healthy. The closer this ratio is to zero, the greater the degree of pathology (e.g. cancer) is believed to be present in the organ. The control block 2 monitors the current via the measurement block 6 and displays the test result on the LCD display 37 on a disease percentage scale until the operator presses the foot pedal 12. The control block stores the test result in the data storage block 3, and activates the buzzer 36 to indicate the completion of the test.

The control unit 2 consists of a microcontroller 16 (typically an 8051). An oscillator 28 provides a clock signal for the microcontroller 16. A standard adress latch (11) configuration is used to create a 16 bit adress bus (11.1,16.3) which connects to 32K random access memory 56 and 32K read only memory 57. A bidirectional data bus 16 1 transports data to and from the microcontroller 16. The microcontroller 16 interfaces which a keypad 9 using keypad interface 17, (typically 74HC922)

The electrodes are galvanically isolated 55 from the main circuit by a transformer 43 in the voltage generator block 5. The measurement block 6 is optically isolated from the main circuit by optocouplers 51,52,53,54. A sinusoidal voltage applied to the primary coil of transformer 43.1 is stepped up by the secondary coil 43.2. Voltage doubling circuit 44 doubles and rectifies the sinusoidal output of coil 43.2 so that a constant voltage appears over capacitor 38. When relay 40 is off an alternating voltage is fed through to the relay 42. When relay 40 is on, the constant voltage over capacitor 38 is fed through to the relay 42. Relay 42 is used to switch the polarity of the signal from relay 40. This combination of relay 42 and 40 is used to set the voltage between the probes to an alternating voltage or a constant voltage and allows the polarity of the probes to be reversed.

The primary coil 43.1 of then transformer 43 is driven by an opamp 41 which is used in inverter amplifier mode. A programmable sinewave generator 39 (typically ML2036) provides the input signal to the opamp 41. Sinewave generator 39 is controlled by the microcontroller 16 via lines 22.1, 22.3, 22.4. The frequency is digitally programmed via this serial bus. The magnitude of the output sinusoidal signal (half peak to peak) is equal to the voltage on the output 24.1 of a digital to analogue converter 24. The output voltage of the digital to analogue converter 24 is set via bus 16.1 by the microcontroller 16.

The current is measured using the measurement block 6. When the circuit between the electrodes is closed by an impedance such as the human body, current is conducted through the electrodes to ground via measuring resistor 46. The voltage appearing over this resistor with respect to ground is therefore proportional to the current through the probes. An opamp buffer 45 feeds the signal to the precision rectifier formed by the opamps referred to by numerals 47 and 48.These extract the absolute value of the signal which is fed into a serial analogue to digital converter (ADC) 49. The ADC 49 communicates with the microcontroller 16 via a serial bus consisting of lines 22.1, 22.2 and 22.3 through an optical link provided by three optocouplers 52,53,54. A zero crossing detector 50 detects the polarity of the voltage over the measuring resistor 46 and transmits this information as a binary one or zero to the microcontroller 16 through an optocoupler 51. When an alternating voltage is applied to the electrodes, current is measured at every voltage peak. The microcontroller 16 waits for a zero to one transition to occur on the output 22.5 of optocoupler 51. The microcontroller 16 waits for a time period equal to one quarter of the period of the output voltage frequency before requesting a conversion from the analogue to digital converter 49.

The microcontroller displays relevant information on a monitor through the video display unit 13. A dual port ram 30 contains a bit mapped version of the screen. The microcontroller 16 can read and write data to the dual port ram 30 through a data bus 16.1 using control lines 16.6 and 16.7 and the adress bus, referred to by numerals 11.1 and 16 3. A field programmable gate array (FPGA) 25 uses counters and shift registers to sequentially read bytes of screen data and to write red green and blue (RGB) pixel information as well as vertical and horizontal retrace information to an RGB to PAL encoder 31. A universal sync generator 33 generates PAL video standard synchronization pulses. These pulses are locked to the mail system clock using a phase locked loop 34. The pixel clock is derived from the main system clock 16.5 using counters in the FPGA 25. The pixel clock is used to read and serialize data at the correct rate and in the correct manner from the dual port ram 30 so that the bit streams fed to the RGB to PAL encoder can be encoded into a PAL standard composite sync video signal that can be fed directly into the video input 31.1 of a standard video monitor.

The UHF modulator unit 10 converts the composite sync video signal to an ultra high frequency signal that can be directly fed into the aerial port 35.1 of a television set. An integrated UHF modulator 35 modulates the composite sync PAL signal from the video display unit to a frequency determined by external components.

Power is delivered to the circuit by the power supply block 4. A transformer 14.1 with primary coupling connected to mains and secondary coupling connected to rectifier bridge 14.2 converts the mains 220VAC to 7.2 VAC. The output of the rectifier is fed into 5V regulator 14.3. A monolithic voltage inverter 15.1 typically a MAX660 generates a −5V supply from the main 5V supply.

The power supplied to the voltage generator block 5 and the measurement block 6 is galvanically isolated from the main power supply. DC to DC converter 15.2 (typically NMA0505) is used to supply +5V and −5SV to the isolated patient interface circuitry.

Figure 10:
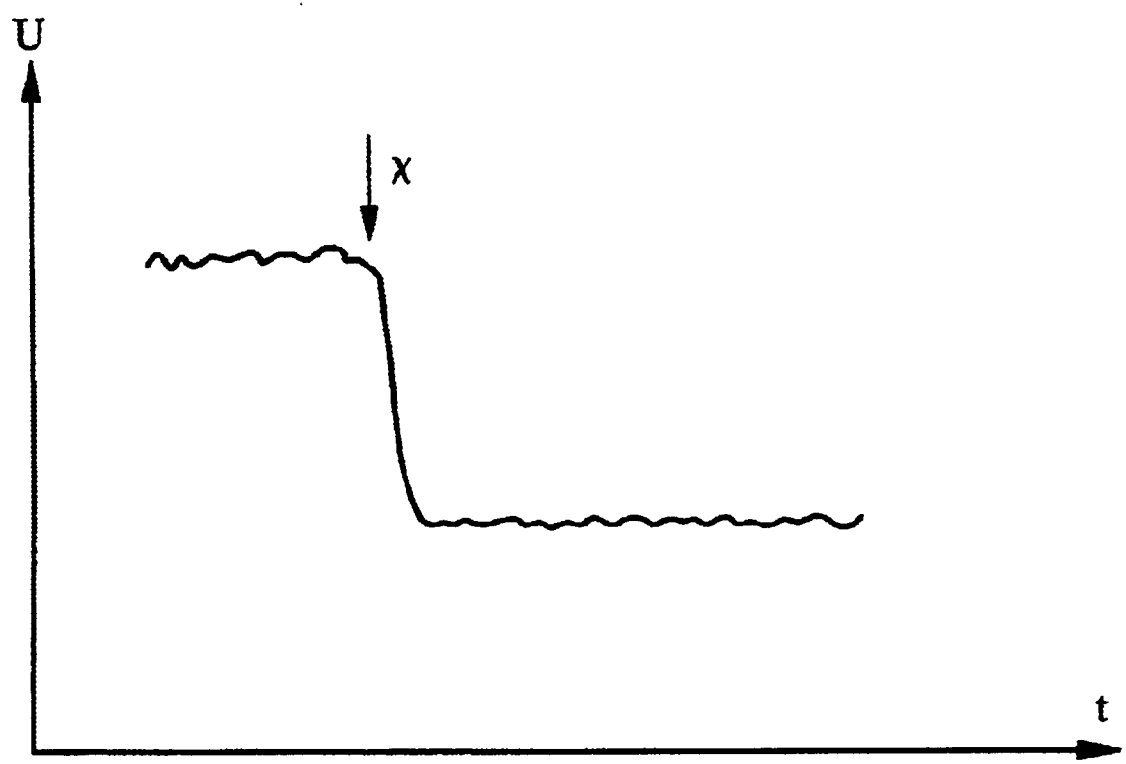
FIG. 10 shows, in graphic representation, the breakthrough effect obtained using the apparatus of the invention in DC measurement mode.

FIG. 10 shows a graph of voltage over a period of time when the breakthrough effect (x) is achieved. At the point of breakthrough (x) a sudden and significant decrease in resistance occurs, and thus a sudden and significant decrease in voltage is also observed. The reference value is measured once the voltage stabilises after the breakthrough effect.

Figure 11A:
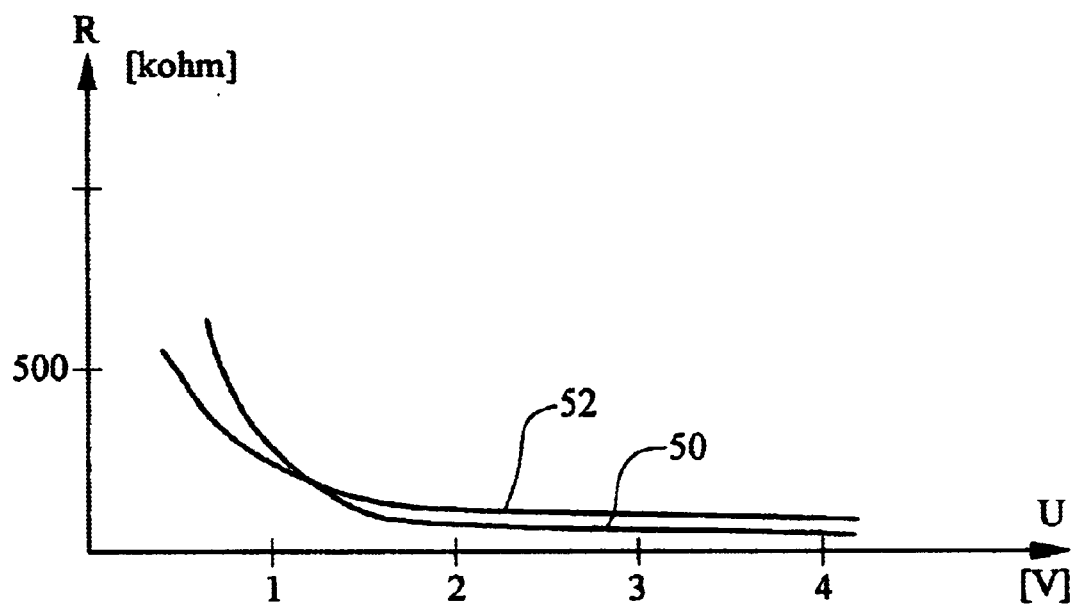
FIG. 11 shows, in graphic representation, the dependence of skin resistance on applied voltage for a skin spot corresponding to a healthy organ (FIG. 11a) and a skin spot corresponding to a diseased organ (FIG. 11b), obtained when applying the technique of the invention using the DC measurement technique.
Figure 11B:
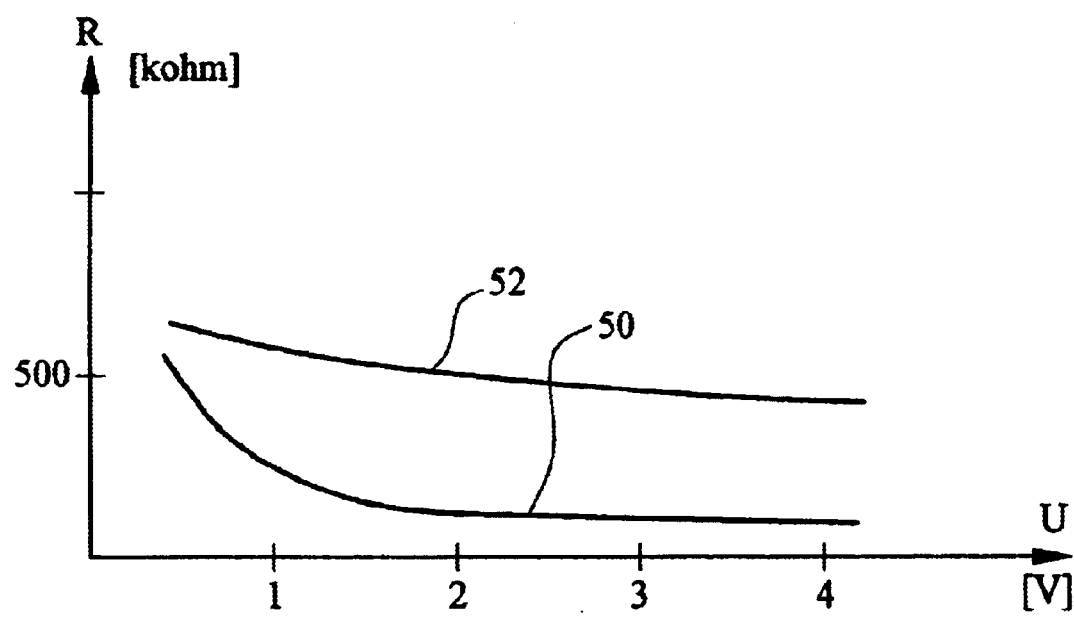

FIGS. 11a and 11b show how resistance is affected when an organ is diseased. In FIG. 11a, the two curves represent resistance values at different voltages for a healthy organ, while FIG. 11b shows two curves of resistance values at different voltages for an unhealthy organ. Lines 50 represent the reference resistance values, and lines 52 represent the measurement resistance values. FIG. 11b shows two curves of resistance values at different voltages for an unhealthy organ. When an organ is healthy, the reference and measurement resistance values are similar, but as the state of disease of the organ increases, so the measurement value increases and the greater the difference between the reference and measurement values.

Figure 12:
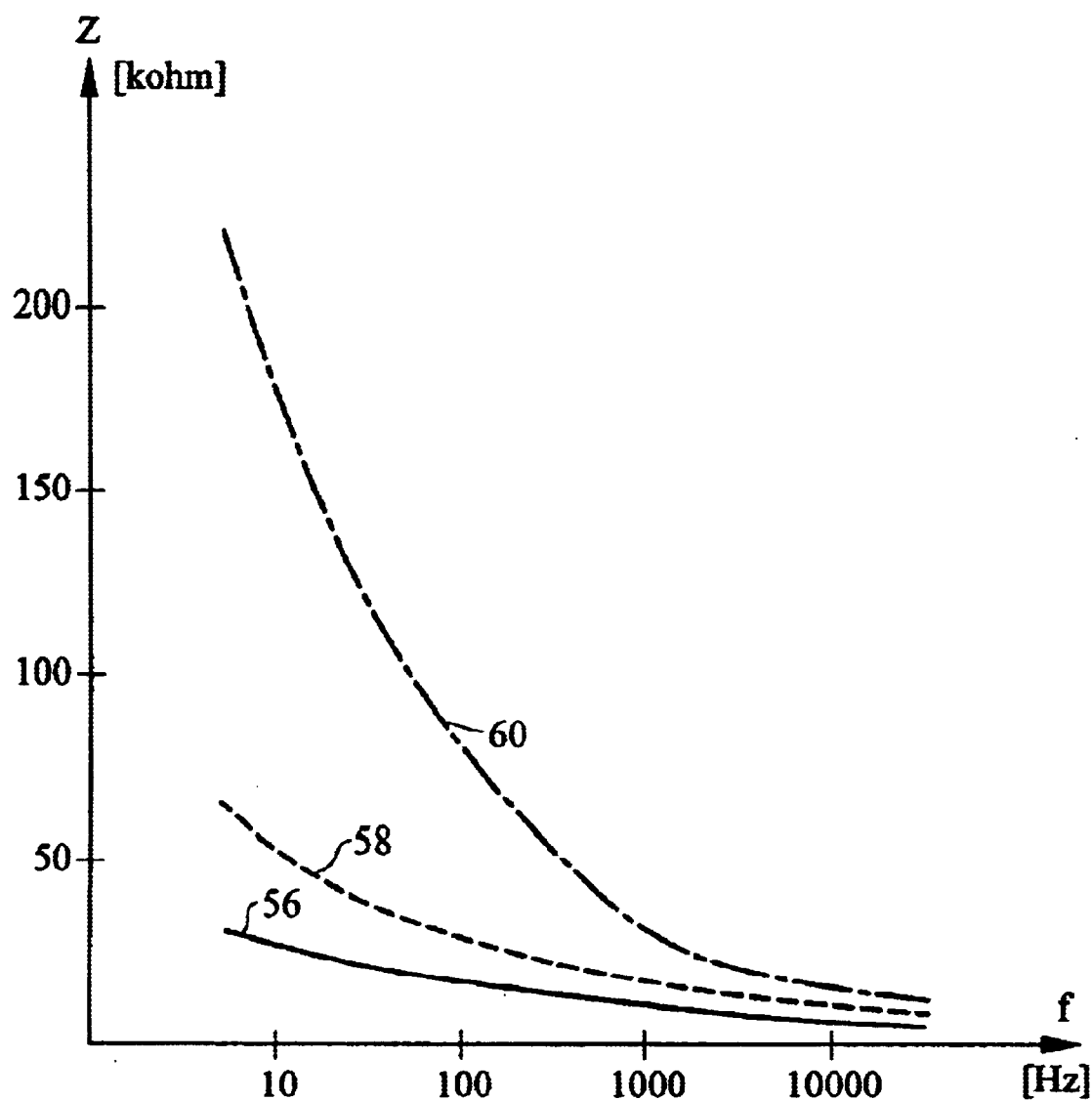
FIG. 12 shows, in graphic representation, the dependence of skin impedance on applied frequency, when applying the technique of the invention using the AC measurement technique.

Similarly, FIG. 12 shows how the measurement impedance changes when an organ is diseased. Line 56 shows reference or resistance values at different frequencies. Line 58 shows measurement resistance values for a healthy organ, whereas line 60 shows measurement resistance values for an unhealthy organ. The more diseased an organ becomes, the higher the resistance of the measurement values, and consequently the greater the difference between the measurement and reference values.

Figure 13:
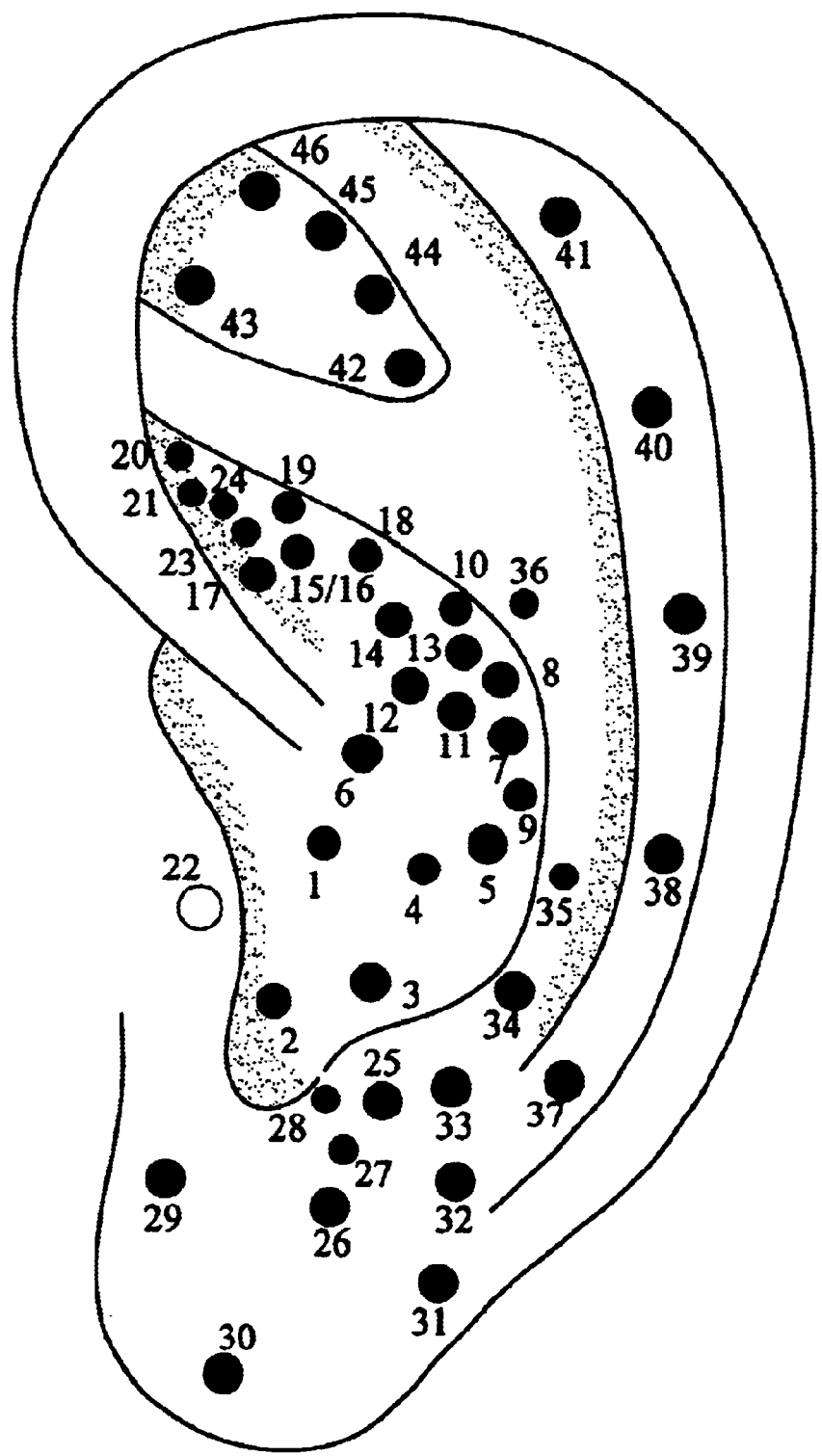
FIG. 13 shows, in graphic representation, skin spots on a human ear auricle corresponding to internal organs.
Figure 14:
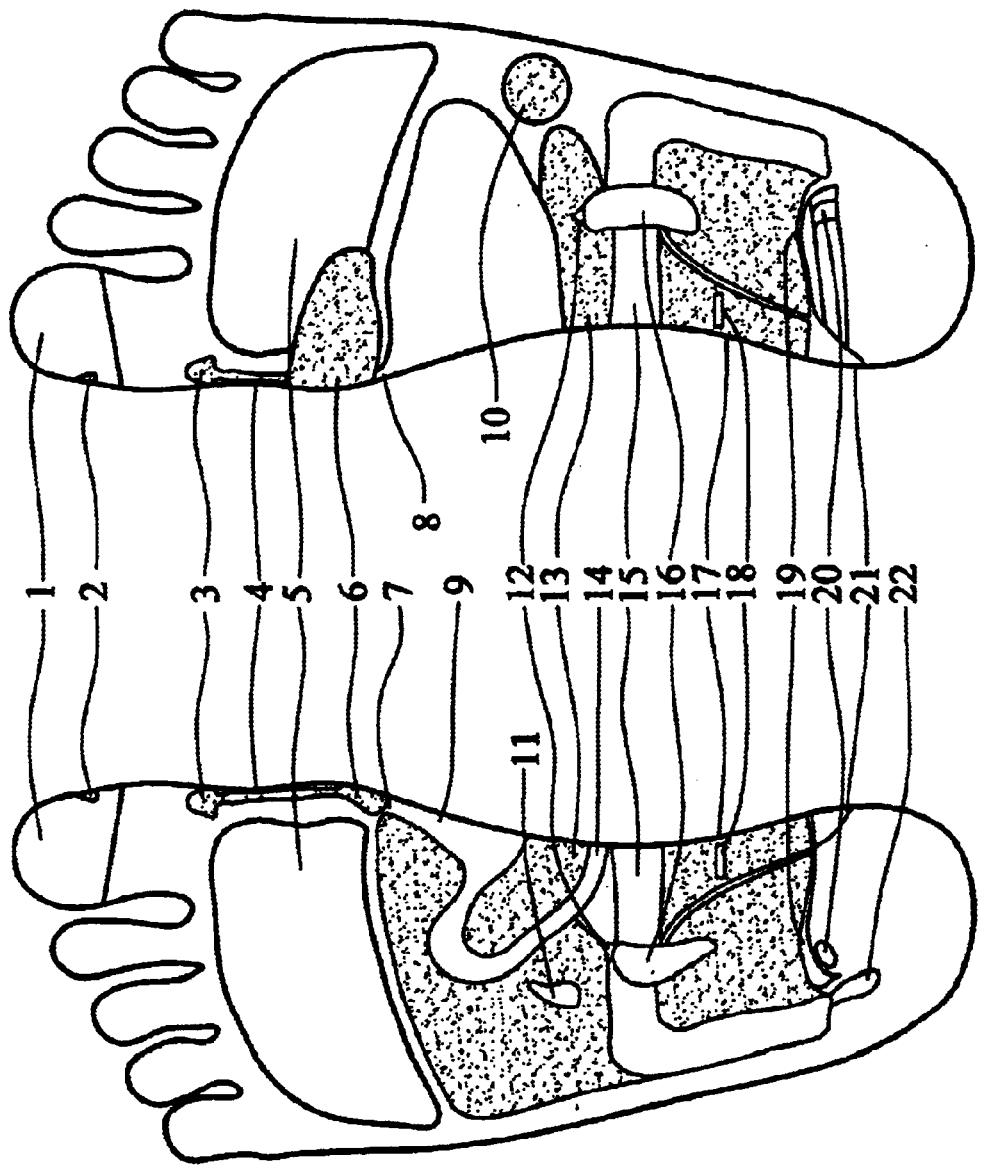
FIG. 14 shows, in graphic representation, skin zones on the sole of a human foot corresponding to particular internal organs.

Referring to FIGS. 13 and 14, the measurement or calibration electrodes are placed on one of the spots indicated in order to obtain a diagnosis of a specific organ. The spot on which the electrode is placed depends on the specified organ, and Tables 1 and 2 set out below show the organs to which the numbered spots refer.

TABLE 1

| Number on FIG. 13 | Portion of Body |
|---|---|
| 1 | Heart (R) |
| 2 | Thyroid Gland |
| 3 | Lungs (Upper Lobe) |
| 4 | Lungs |
| 5 | Oesophagus (Cardia) |
| 6 | Stomach |
| 7 | Liver (Left Lobe) (R) |
| 8 | Liver (Right Lobe) (L) |
| 9 | Spleen (R) |
| 10 | Kidneys |
| 11 | Pancreas (R) |
| 12 | Gall Bladder (L) |
| 13 | Duodenum (L) |
| 14 | Transverse Colon |
| 15 | Left Colon (R) |
| 16 | Right Colon (Appendix) (L) |
| 17 | Small Intestine |
| 18 | Ureter |
| 19 | Bladder |
| 20 | Prostate |
| 21 | Distal Colon |
| 22 | Mammary Gland |
| 23 | Ovary & Adnexa Uteri |
| 24 | Uterus |
| 25 | Pons |
| 26 | Thalamus |
| 27 | Hypothalamus |
| 28 | Hypophysis |
| 29 | Cortex (Frontal Lobe) |
| 30 | Midcortex |
| 31 | Cortex (Posterior) |
| 32 | Cerebellum |
| 33 | Medulla Oblongata |
| 34 | Cervical Spine |
| 35 | Thoracic Spine |
| 36 | Lumbo-Sacral Spine |
| 37 | Shoulder |
| 38 | Elbow |
| 39 | Wrist |
| 40 | Metacarpus |
| 41 | Fingers |
| 42 | Hip |
| 43 | Knee |
| 44 | Ankle |
| 45 | Metatarsus |
| 46 | Toes |

(L)-left ear auricle
(R)-right ear auricle

TABLE 2

| Number on FIG. 14 | Portion of Body |
|---|---|
| 1 | Brain |
| 2 | Pituitary |
| 3 | Thyroid Gland |
| 4 | Oesophagus |
| 5 | Lungs |
| 6 | Heart |
| 7 | Liver |
| 8 | Cardiac Sphincter |
| 9 | Stomach |
| 10 | Spleen |
| 11 | Gall Bladder |
| 12 | Adrenal Glands |
| 13 | Pancreas |
| 14 | Duodenum |
| 15 | Colon |
| 16 | Kidneys |
| 17 | Small Intestine |
| 18 | Ureters |
| 19 | Fallopian Tubes |
| 20 | Ovaries |
| 21 | Bladder |
| 22 | Appendix |

The invention is not limited to the precise constructional details disclosed in this specification and it will be clear to those skilled in the art that the above principles may be applied to produce other apparatus embodying these principles. Specifically, the apparatus as described uses impedance and resistance measurements to calculate the state of health of the organ in question, but it will be clear to those skilled in the art that other values which are either directly or indirectly proportional to resistance or impedance may be used as measurements and in the calculations.

What is claimed is:

1. An apparatus for diagnosing a state of health of an organ in a human or animal body, the apparatus including:

an electrical generator;

a measurement electrode and a reference electrode, for connection, in use, to the generator;

means for monitoring and measuring at least a first parameter which is dependent upon resistance or impedance between the electrodes when the measurement electrode is placed in contact with a first zone of skin corresponding to the organ and the reference electrode is placed in contact with a second zone of skin on the same body, and a DC potential difference is applied between the electrodes by the generator, in use;

recording means configured to record a first measured value of the first parameter after a sudden and significant change in the first parameter due to a reduction in resistance of the skin at a breakthrough potential difference;

means for changing the potential difference between the electrodes such that the polarity of the electrodes is inverted after the first measured value has been recorded;

recording means configured to record a second measured value of a second parameter which is dependent upon resistance or impedance between the electrodes after inverting the polarity of the electrodes; and means for comparing the first and second measured values to obtain a third value which is an indicator of the state of health of the organ to which the first zone of skin corresponds.

2. An apparatus as claimed in claim 1, wherein the measurement electrode is negatively polarized with respect to the reference electrode while the first parameter is monitored, measured, and recorded.

3. An apparatus as claimed in claim 1, wherein the measurement electrode is a point electrode having a relatively small skin-contactable surface area.

4. An apparatus as claimed in claim 1, which includes means for adjusting the current or potential difference to cause the sudden and significant change in the first parameter, due to a reduction in resistance of the skin at the breakthrough potential difference.

5. An apparatus as claimed in claim 1, which includes a display means for indicating the first zone of skin onto which the measurement electrode should be placed in order to obtain a diagnosis for a particular organ.

6. An apparatus as claimed in claim 5, wherein the display means indicates zones of skin which are located on a foot or an ear.

7. An apparatus as claimed in claim 1, wherein the third value is expressed as a ratio of the first and second measured values.

8. An apparatus as claimed in claim 1, which includes communication means for communicating, to an operator of the apparatus, the state of health of the diagnosed organ as being either healthy, normal, sub-acute or acute, depending on the third value.

9. A method for diagnosing a state of health of an organ in a human or animal body, the method including the steps of:

placing a measurement electrode on or near a zone of skin which corresponds to the organ and placing a reference electrode in contact with another zone of skin of the same body;

monitoring and measuring at least a first parameter which is dependent upon resistance or impedance between the electrodes when a DC potential difference is applied between the electrodes;

recording a first measured value of the first parameter after a sudden and significant change in the first parameter due to a reduction in resistance or impedance of the skin at a breakthrough potential difference;

changing the potential difference between the electrodes such that the polarity of the electrodes is inverted after the first measured value has been recorded;

recording a second measured value of a second parameter which is dependent upon resistance between the electrodes after inverting the polarity of the electrodes; and comparing the first and second measured values to obtain a third value which is an indicator of the state of health of the organ to which the first zone of skin corresponds.

10. A method as claimed in claim 9, the potential difference applied between the electrodes is such that the measurement electrode is negatively polarized with respect to the reference electrode while the first parameter is monitored, measured, and recorded.

11. A method as claimed in claim 9, wherein the measurement electrode is a point electrode having a relatively small skin-contactable surface area.

12. A method as claimed in claim 9, which includes the step of adjusting the potential difference to cause the sudden and significant change in the first parameter, due to a reduction in resistance of the skin at the breakthrough potential difference.

13. A method as claimed in claim 9, wherein the third value is expressed as a ratio of the first and second values.

14. A method as claimed in claim 9, wherein the measurement electrode is placed on an outer ear, or on a sole of a foot, having the zone of skin which corresponds to the organ.

15. A method as claimed in claim 14, which includes the step of using a display means which indicates the zone of skin of a foot or an ear onto which the measurement electrode should be placed in order to obtain a diagnosis for a particular organ.

* * * * *